(12) United States Patent
Wang et al.

(10) Patent No.: US 8,614,787 B2
(45) Date of Patent: Dec. 24, 2013

(54) HIGH THROUGHPUT QUANTUM EFFICIENCY COMBINATORIAL CHARACTERIZATION TOOL AND METHOD FOR COMBINATORIAL SOLAR TEST SUBSTRATES

(75) Inventors: Yun Wang, San Jose, CA (US); Tony P. Chiang, Campbell, CA (US); Chi-I Lang, Cupertino, CA (US)

(73) Assignee: Intermolecular, Inc., San Jose, CA (US)

( * ) Notice: Subject to any disclaimer, the term of this patent is extended or adjusted under 35 U.S.C. 154(b) by 392 days.

(21) Appl. No.: 12/952,855

(22) Filed: Nov. 23, 2010

(65) Prior Publication Data
US 2011/0279810 A1 Nov. 17, 2011

Related U.S. Application Data

(60) Provisional application No. 61/334,165, filed on May 12, 2010.

(51) Int. Cl.
*G01N 21/00* (2006.01)
(52) U.S. Cl.
USPC .......................................................... 356/72
(58) Field of Classification Search
USPC .................................................... 356/72–73
See application file for complete search history.

(56) References Cited

U.S. PATENT DOCUMENTS 4,880,349 A * 11/1989 Woodward ...................... 29/743
2012/0010854 A1 * 1/2012 Ciocan et al. ................. 702/182

OTHER PUBLICATIONS

Ciocan, R. et al., System for High Accuracy Internal Quantum Efficiency Measurement, IEEE, 978-1-4244-2950-9/09 (2009), pp. 1862-1864.*
Fischer, B., Scanning IQE-Measurement for Accurate Current Determination on Very Large Area Solar Cells, IEEE, 0-7803-7471-1/02 (2002), pp. 454-457.*
Newport Corporation, Oriel IQE-200, Product Description, Nov. 8, 2009 [retrieved on Jan. 15, 2013]. Retrieved from the Internet, Wayback Machine at www.archive.org.*
Newport Corporation, Oriel IQE-200, Product Detail, Nov. 12, 2009 [retrieved on Jan. 15, 2013]. Retrieved from the Internet, Wayback Machine at www.archive.org.*
Newport Corporation, Oriel IQE-200, Specifications, Nov. 11, 2009 [retrieved on Jan. 15, 2013]. Retrieved from the Internet, Wayback Machine at www.archive.org.*
Newport Corporation, Oriel IQE-200, Drawings, Nov. 12, 2009 [retrieved on Jan. 15, 2013]. Retrieved from the Internet, Wayback Machine at www.archive.org.*
Newport Corporation, Oriel IQE-200, 2009 Product Introduction, Jan. 3, 2010 [retrieved on Jan. 15, 2013]. Retrieved from the Internet, Wayback Machine at www.archive.org.*
Newport Corporation, SMC100 Data Sheet, Dec. 2005 [retrieved on Jan. 16, 2013]. Retrieved from the Internet, http://assets.newport.com/webDocuments-En/images/SMC100_Data_Sheet_MC.pdf.*

* cited by examiner

*Primary Examiner* — Kara E Geisel

(57) ABSTRACT

Simultaneous measurement of an internal quantum efficiency and an external quantum efficiency of a solar cell using an emitter that emits light; a three-way beam splitter that splits the light into solar cell light and reference light, wherein the solar cell light strikes the solar cell; a reference detector that detects the reference light; a reflectance detector that detects reflectance light, wherein the reflectance light comprises a portion of the solar cell light reflected off the solar cell; a source meter operatively coupled to the solar cell; a multiplexer operatively coupled to the solar cell, the reference detector, and the reflectance detector; and a computing device that simultaneously computes the internal quantum efficiency and the external quantum efficiency of the solar cell.

19 Claims, 11 Drawing Sheets

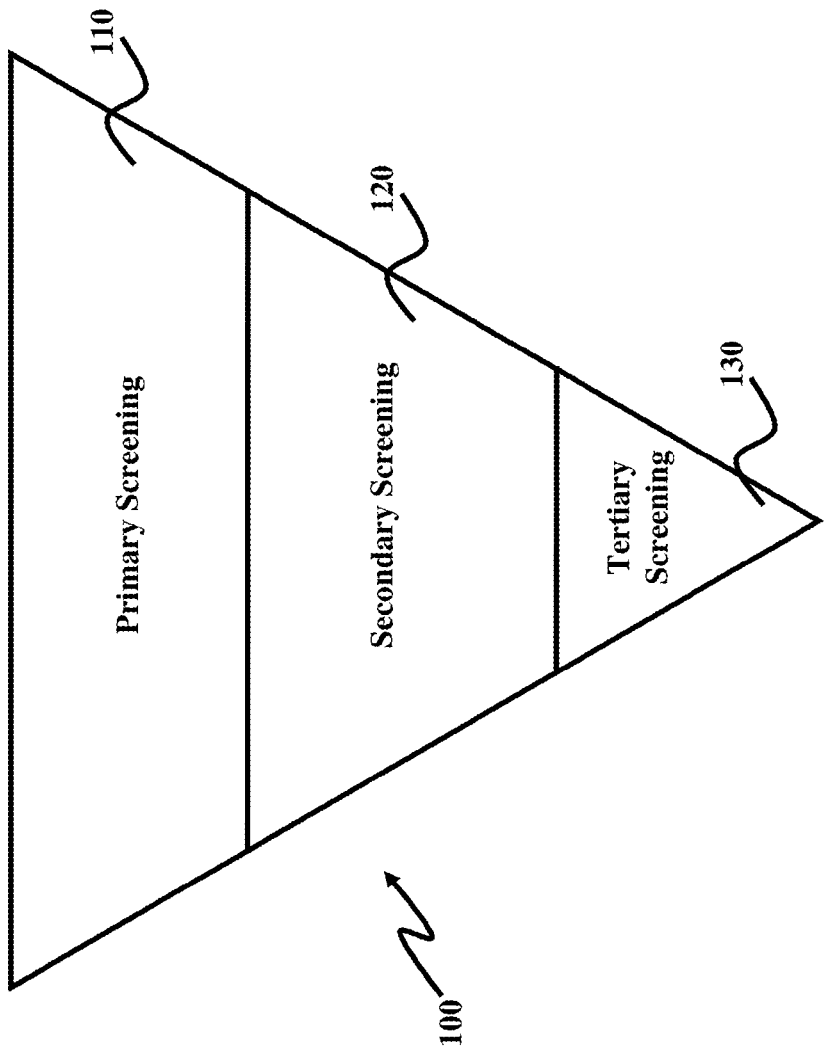

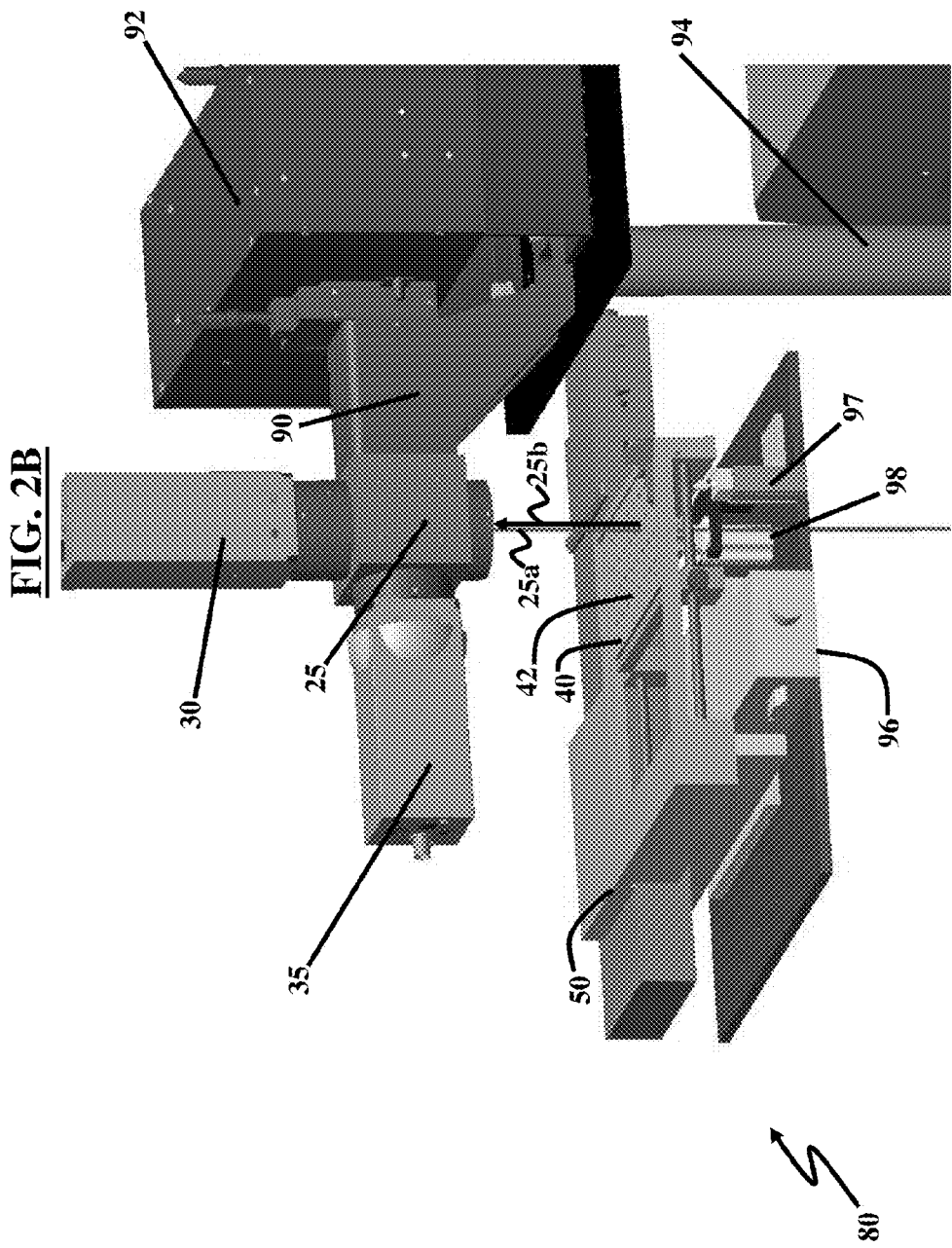

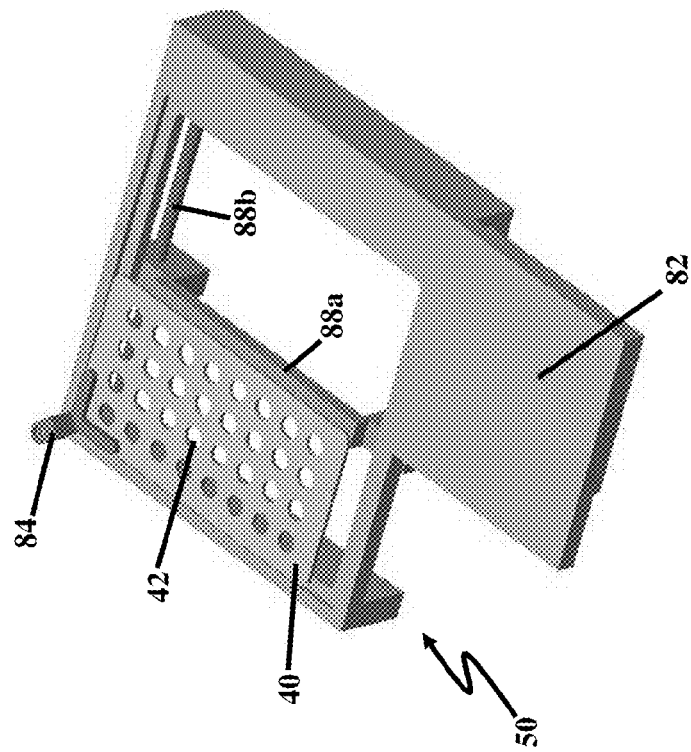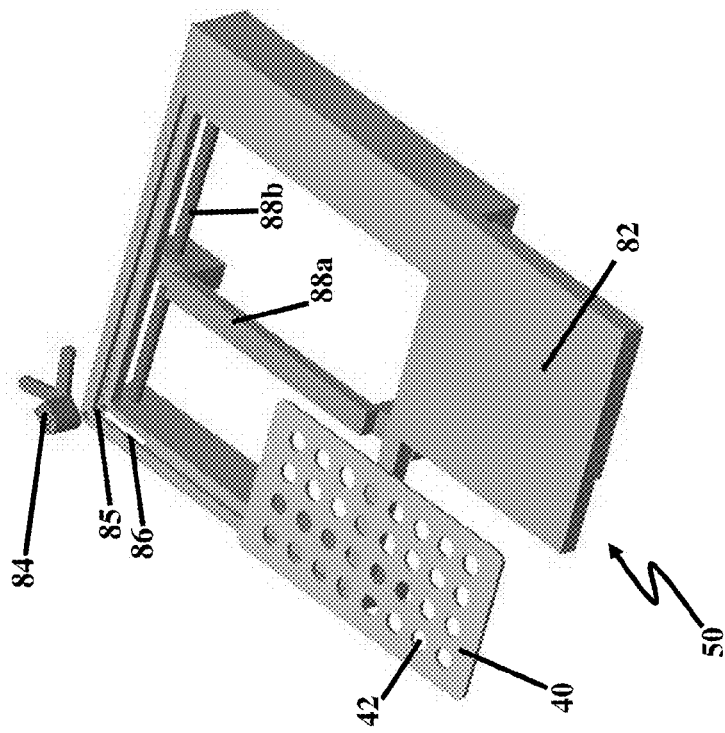

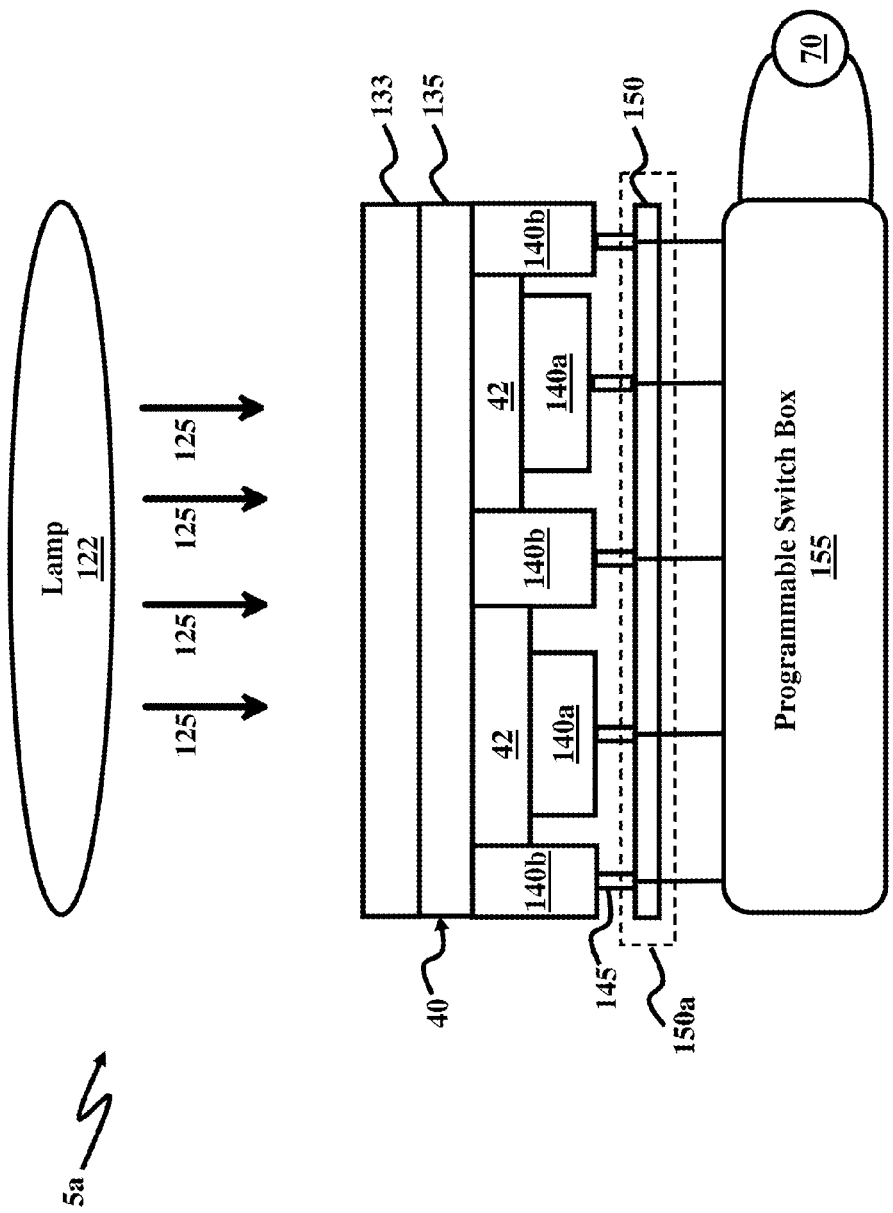

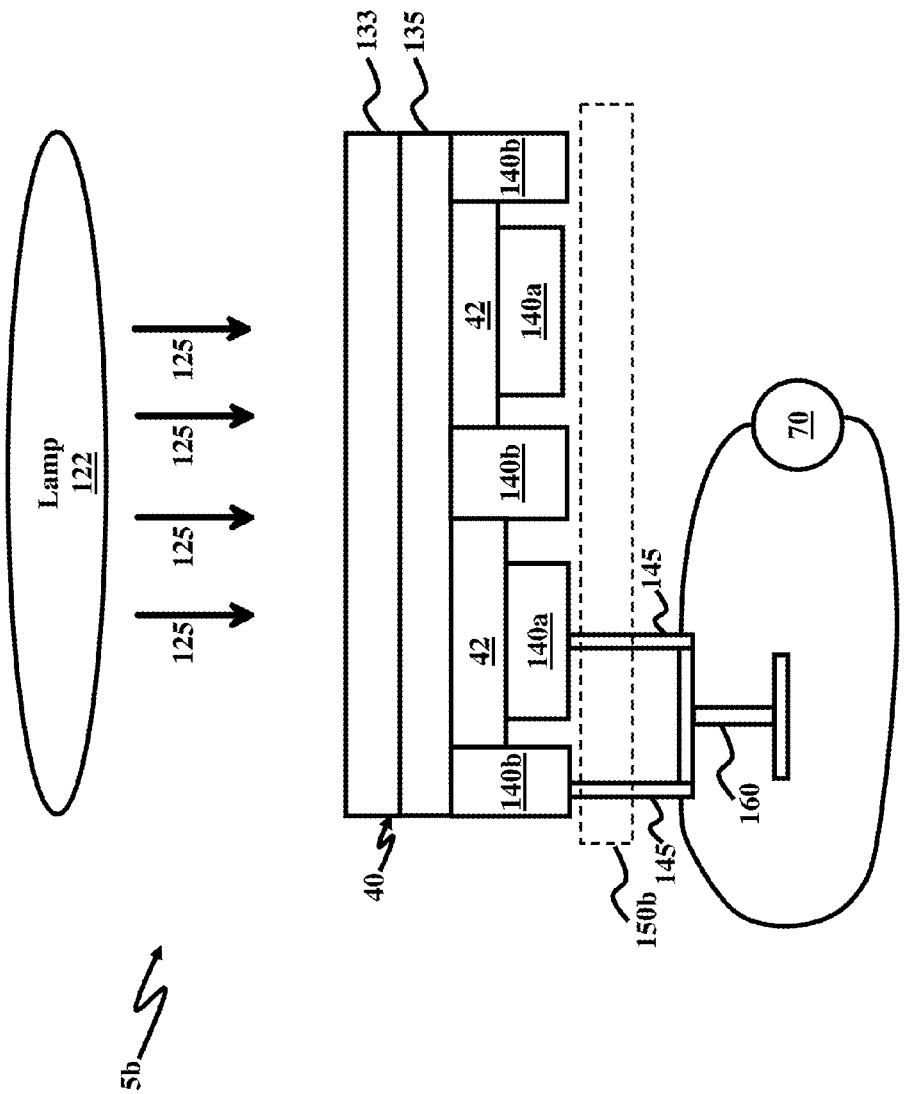

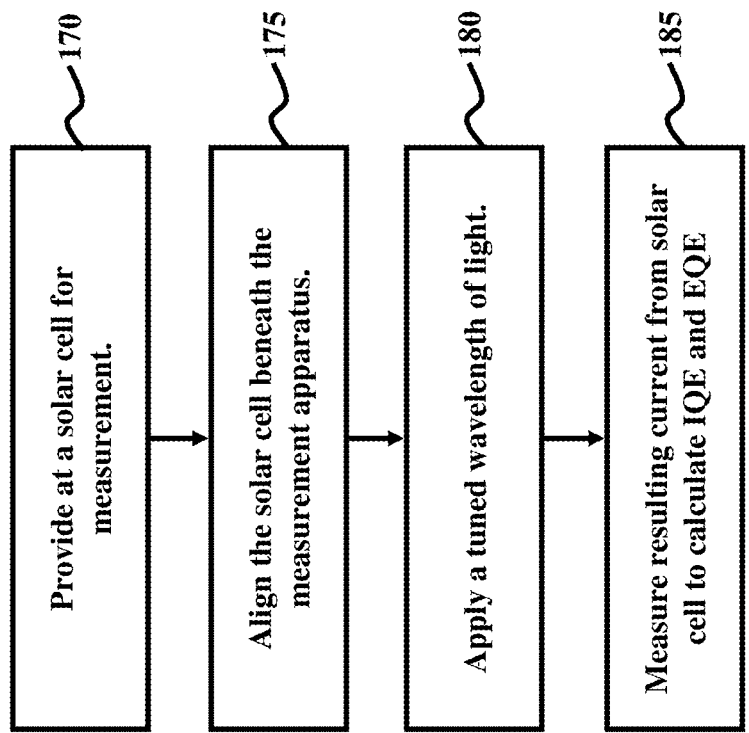

HIGH THROUGHPUT QUANTUM EFFICIENCY COMBINATORIAL CHARACTERIZATION TOOL AND METHOD FOR COMBINATORIAL SOLAR TEST SUBSTRATES

CROSS-REFERENCE TO RELATED APPLICATION

This application claims priority to U.S. Provisional Patent Application No. 61/334,165, filed May 12, 2010 and entitled "High Throughput Combinatorial Characterization Tool for Combinatorial Solar Test Substrates," the contents of which, in its entirety, is herein incorporated by reference.

BACKGROUND

1. Technical Field

The embodiments herein generally relate to solar processing and characterization, and more specifically, to a high throughput combinatorial characterization tool for combinatorial test substrates.

2. Description of the Related Art

Some exemplary solar processing operations include operations for adding (depositions) and removing layers (etch), defining features, preparing layers (e.g., cleans), doping, etc. However, solar companies conduct research and development (R&D) on full substrate processing, often on very large substrates and requiring a complete solar cell manufacturing line. This approach has resulted in high R&D costs and the inability to conduct extensive experimentation in a timely and cost effective manner. Combinatorial processing as applied to solar manufacturing operations enables multiple experiments to be performed on a single substrate and without a complete solar cell manufacturing line. Equipment for performing the combinatorial processing and characterization of the combinatorial test substrates must support the efficiency offered through the combinatorial processing operations.

Combinatorial processing enables rapid evaluation of solar processing operations. The systems supporting the combinatorial processing are flexible to accommodate the demands for running the different processes either in parallel, serial, or some combination of the two. A valuable component of the systems for combinatorial processing are the characterization tools used to produce the data from high throughput experimentation in such a way that the process does not slow down. High performance combinatorial characterization tools are needed to quickly process and characterize the combinatorial test substrates.

Conventional solar electrical characterization such as internal quantum efficiency and external quantum efficiency measurements in a R&D environment is performed independently of one another in a manual and sequential mode. However, the conventional process tends to be time consuming and resource demanding resulting in a significant loss in testing throughput. For example, when there is a need for measuring multiple sites per sample, the throughput and resources of the operators becomes a critical issue. Taking 32 sites per sample as an example, it takes 30 minutes to measure the external quantum efficiency (EQE) per site. To finish the characterization of each example, the operator has to move the sites every 30 minutes for the next 16 hours. It is a lengthy and tiring test.

BRIEF DESCRIPTION OF THE DRAWINGS

The embodiments herein will be better understood from the following detailed description with reference to the drawings, in which:

FIG. 1 illustrates a schematic diagram of a combinatorial screening process according to an embodiment herein;

FIG. 2B illustrates a schematic diagram of a quantum efficiency measurement tool according to an embodiment herein;

FIG. 3A illustrates a schematic diagram of an unloaded sample tray according to an embodiment herein;

FIG. 3B illustrates a schematic diagram of a loaded sample tray according to an embodiment herein;

FIG. 4B illustrates a block diagram of a multi-pin combinatorial characterization apparatus according to an embodiment herein;

FIG. 4C illustrates a block diagram of a Z-stage combinatorial characterization apparatus according to an embodiment herein;

FIG. 5 illustrates a flowchart of a method according to an embodiment herein.

DETAILED DESCRIPTION OF THE DRAWINGS

Figure 2A:
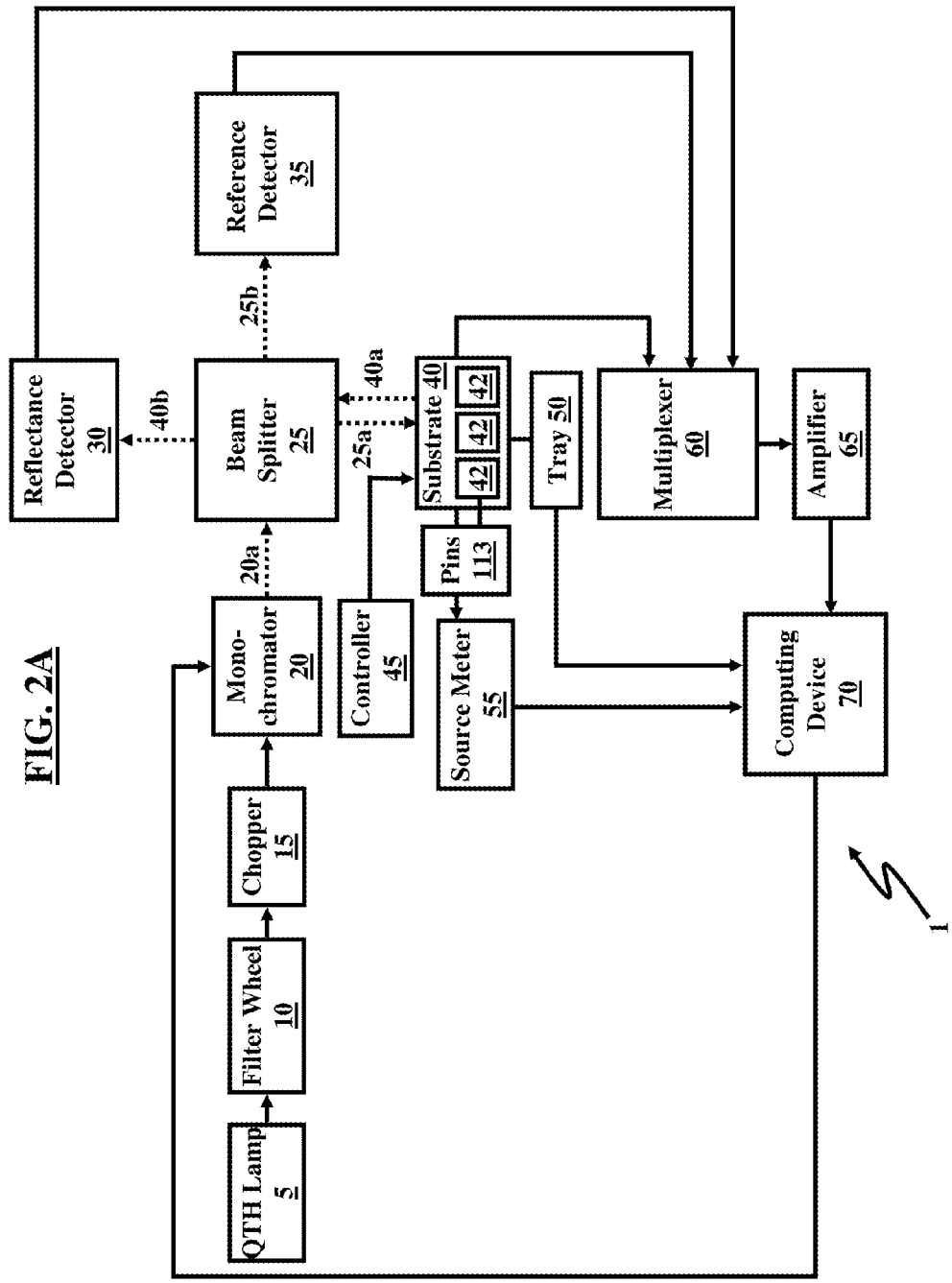
FIG. 2A illustrates a block diagram of a quantum efficiency apparatus according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

With increasing energy demands, alternative (e.g., green) energy gains more and more attention. As an important part of the research and development of solar cells, the electrical characterization of those solar cells also needs to improve. Measurement of the quantum efficiency of a solar cell is a valuable parameter to judge the cell performance. It determines how efficiently the solar energy can be converted into electricity. Quantum efficiency may be characterized by measuring the current-voltage (I-V) curve of the cell under standard one sun illumination. In the lab test environment, a solar simulator is used as the light source with less than 1% spectrum difference as actual sunshine. The current generated by an illuminated solar cell is measured as the voltage scan by connecting the electrodes of the cell to a source meter.

The embodiments herein provide a high performance combinatorial characterization tool that saves both operator resources as well as test time, and offers a key function for high throughput and combinatorial research. Referring now to the drawings, and more particularly to FIGS. 1 through 6, where similar reference characters denote corresponding features consistently throughout the figures, there are shown several embodiments.

Combinatorial processing systems are only as good as the characterization available. Therefore, the high performance characterization tool described herein provides the means by which true high throughput experimentation may be accomplished. The operator burden can be minimized by test automation. The test time can be significantly reduced by parallel testing by measuring multiple sites at the same time instead of measuring one at a time. Although the high performance characterization tool described herein exhibits extraordinary utility in the field of combinatorial processing (e.g., by enabling high throughput experimentation), the embodiments herein, however, are not limited to combinatorial processing. Thus, the use of the high performance characterization tool described herein in combinatorial processing systems represents one of many valuable applications of the embodiments herein. For example, traditional solar cell experimentation and exploration methods, semiconductor manufacturing and fabrication, light emitting diode (LED) applications, flat panel display applications, characterization of photochromic materials, characterization of electrochromic materials, and characterization of thermochromic materials, among other applications, would all benefit from the high throughput and rapid characterization offered by the high performance characterization tool described herein.

As described above, during one embodiment of combinatorial processing, each wafer is subjected to many different process conditions. FIG. 1 illustrates an example of such a combinatorial screening process. As shown in FIG. 1, combinatorial screening process 100 includes primary screening process (110), secondary screening process (120), and tertiary screening process (130). In FIG. 1, for example, numerous material compositions (e.g., 18 spots or 46 spots on a single wafer, where each spot is a unique material composition) are systematically explored on a single wafer during an initial primary screening process (110) at speeds that would otherwise be impossible using traditional methods and tools. In other words, in the embodiment shown in FIG. 1, primary screening process (110) is an initial screening that processes many samples to rule out materials for further screening. Once the best materials, process conditions, or process integration are identified using initial combinatorial screening methods (e.g., during primary screening process (110)), that material is then scaled up to test the performance (e.g., EQE and IQE performance) of that material and/or conditions during a secondary screening stage (e.g., secondary screening process (120)). Furthermore, according to one embodiment herein, additional testing may take place during tertiary screening process (130). During tertiary screening process (130), for example, the materials and/or process conditions that were not filtered out during primary screening process (110) and secondary screening process (120) are scaled up to a full-scale device size. Furthermore, due to the speed and non-destructiveness of the performance test (described in further detail below) occurring in secondary screening process (120), materials and/or conditions that pass both the primary screening process (110) and secondary screening process (120) can rapidly proceed to tertiary screening process (130). Consequently, to test the performance of these material compositions, embodiments herein utilize an improved measurement tool to enable the collection of information more rapidly.

FIG. 2A, with reference to FIG. 1, illustrates a block diagram of quantum efficiency apparatus 1 according an embodiment herein. In quantum efficiency apparatus 1, the light spectrum is filtered so that each wavelength of light can be used individually to test the performance of solar cells 42, and in one particular embodiment, the solar cells 42 may be individual site-isolated devices on a combinatorial solar test substrate 40 where each of the site-isolated devices has been varied as compared to one another. In alternate embodiments, the substrate 40 being tested may be a substrate 40 having multiple unvaried solar cells 42 produced for either commercial or research and development purposes. For purposes of discussion only, examples of a solar test substrate 40 include, but are not limited to: copper indium gallium diselenide (CIGS), copper zinc tin sulfide (CZTS), and other thin film photovoltaic (TFPV) materials with a silicon or glass substrate. Quantum efficiency apparatus 1 measures the reflected light and the transmittance of the light simultaneously in order to determine the amount of light absorbed and converted into electricity by the solar cells 42 in the site-isolated regions. In other words, quantum efficiency apparatus 1 simultaneously measures internal quantum efficiency (IQE) and external quantum efficiency (EQE). EQE is calculated as the ratio of a measured number of charge carriers (e.g., current) collected by a solar cell 42 to the number of photons of a given energy shining on the solar cell 42 from outside (i.e., incident photons). IQE is calculated as the ratio of the number of charge carriers (e.g., current) collected by the solar cell 42 to the number of photons of a given energy that shine on the solar cell 42 from outside and is absorbed by the solar cell 42.

As shown in FIG. 2A, one embodiment of quantum efficiency apparatus 1 includes a quartz tungsten halogen (QTH) lamp 5 (e.g., 1000 W FEL QTH lamp available from Newport Corporation, Irvine, Calif., USA), a filter wheel 10, an optical chopper 15, a monochromator 20, a three-way beam splitter 25, a reflectance detector 30, a reference detector 35, a substrate 40 (which may include one or more solar cells 42 as a specially treated region thereon, as described below), a white light biased controller 45, a sample tray 50, a source meter 55, a multiplexer 60, a lock-in amplifier 65, and a computing device 70. As discussed in further detail below, by using a three-way beam splitter 25, quantum efficiency apparatus 1 measures both incident and reflected light intensity to calculate EQE and IQE simultaneously. Therefore, in contrast with conventional devices, quantum efficiency apparatus 1 does not require a user to remove a sample to obtain a reference light measurement, and quantum efficiency apparatus 1 is able to collect IQE without making any special adjustments to the apparatus 1 and taking a second measurement. Additionally, no adjustments to data obtained from reflectance detector 30 and source meter 55 have to be made because all of the necessary data is collected on quantum efficiency apparatus 1 and the measurements of absorbance and reflectance are made at the same time using computing device 70. Moreover, simultaneous EQE and IQE measurements performed by quantum efficiency apparatus 1 provide improved accuracy over conventional systems by eliminating errors, complication, time, materials, and cost associated with moving a sample from one measuring device to another measuring device.

According to the embodiment shown in FIG. 2A, the combination of QTH lamp 5, filter wheel 10, optical chopper 15, and monochromator 20 produces light 20a at a specific wavelength, to allow precise simultaneous measurement of the EQE and IQE characteristics of solar cell 42. Light 20a is directed to three-way beam splitter 25, where one half of the incoming light is directed to a solar cell 42 within a substrate 40 (e.g., light 25a) and the other half of the incoming light is directed to reference detector 35 (i.e., light 25b). When light 25a hits solar cell 42 (e.g., a CIGS, CZTS substrate, etc.), the reflected light (i.e., light 40a) is directed by three-way beam splitter 25 to reflectance detector 30 (i.e., in the form of light 40b). The amount of light 25a absorbed by the solar cell 42 within the substrate 40 and converted to an electrical current is detected by source meter 55 that is coupled to pins 113 that are in contact with the solar cell 42 and/or substrate 40 (as discussed in further detail below). In addition, according to one embodiment herein, white light bias controller 45 is used to isolate the EQE and IQE response from a single absorption layer (not shown) in solar cell 42 when solar cell 42 is a multi-layer absorption cell by biasing a single layer in solar cell 42 to white light (e.g., natural light).

As further shown in FIG. 2A, light 25b is directed to reference detector 35 and the output of reference detector 35 serves as an input to multiplexer 60. Multiplexer 60 accepts, as input, the output of reflectance detector 30 and the current produced by solar cell 42. Thereafter, lock-in amplifier 65 extracts and amplifies the specific wavelength desired to calculate the EQE and IQE characteristics of solar cell 42 from the inputs of multiplexer 60.

By measuring the incoming light 20a (via reference detector 35) for each test (e.g., through multiplexer 60), the accuracy of the resulting data is increased because the light source intensity and wavelength is determined (e.g., on computing device 70) at the same time as the absorbed light (e.g., from solar cell 42) and the reflected light (e.g., from reflectance detector 30) for each solar cell 42 on substrate 40. In addition, computing device 70 may include elements described in FIG. 6, and further described below, in order to perform its calculations and processing. In contrast to a traditional testing method, where the incoming light is only tested at the beginning before conducting a test on the entire substrate, quantum efficiency apparatus 1 tests incoming light (e.g., light 20a) of each solar cell 42 on substrate 40 at the same time as the other light measurements (absorbance and reflectance). Using reference detector 35 allows quantum efficiency apparatus 1 to identify any drift in the wavelength between tests of each solar cell 42. Moreover, using reference detector 35 improves the accuracy of the measurements and further improves the uniformity and accuracy of testing multiple solar cells 42 (e.g., on substrate 40 during combinatorial testing, testing multiple solar cells 42 on multiple substrates 40, and other testing scenarios that involve multiple solar cells 42).

FIG. 2B, with reference to FIGS. 1 and 2A, illustrates a schematic diagram of a quantum efficiency measurement tool 80 according to an embodiment herein. As shown in FIG. 2B, quantum efficiency measurement tool 80 includes three-way beam splitter 25, reflectance detector 30, reference detector 35, substrate 40, sample tray 50, light enclosure 90, emitter 92, support platform 94, articulation platform 96, probe module 97, and transmittance detector 98. Also shown in FIG. 2B is light 25a, which is light originating from emitter 92 after traveling through light enclosure 90 and being split at three-way beam splitter 25. In one embodiment the light 25a coming from the emitter 92 may have all wavelengths of natural sunlight for the testing of solar cells 42. The spectrum of light frequencies of light 25a may be varied depending on the samples being tested, for example there may be applications where infrared or ultraviolet wavelengths may be needed. In one embodiment, emitter 92 also includes QTH lamp 5, filter wheel 10, chopper 15, and monochromator 20 (shown in FIG. 2A). In FIG. 2B, light 25a comprises a focused beam of light from emitter 92 that has been filtered to one wavelength (e.g., via filter wheel 10, shown in FIG. 2A) as is directed over a specific spot on substrate 40 (e.g., on solar cell 42). The focused beam of light covers an area within the solar cell 42 being tested that is smaller than the area of the solar cell 42.

Figure 2C:
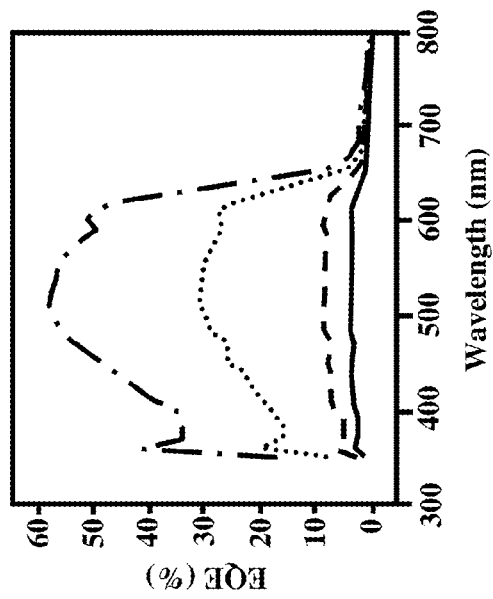
FIG. 2C illustrates a graphical representation of an output curve of a quantum efficiency measurement tool according to an embodiment herein.

Such a small localized beam of light ensures that all of the light hits the particular solar cell 42 being tested and that the beam of light is not affecting neighboring cells. This small localized beam of light within the solar cell 42 improves the consistency of the measurements between different solar cells, which may be valuable when comparing data for combinatorially varied solar cells 42 on a single substrate 40 or even on different substrates. To measure the QE of each of the solar cells 42, the filter wheel 10 cycles the beam of light through all of the wavelengths of light coming from emitter 92 and which, in the example of a solar cell 42, will be wavelengths in the spectrum of natural sunlight. The electrical current produced by the solar cell 42 at each of the wavelengths is measured along via probe module 97 (e.g., using pins 113 shown in FIG. 2A) with the reflected light to determine the quantum efficiency at each of the wavelengths. A set of curves, such as the one illustrated in FIG. 2C, may be generated using this data. As shown in FIG. 2C, the results of four different test configurations/samples are depicted in order to compare the quantum efficiency percentage versus the wavelength for each sample. Different configurations/samples generate different results based on the particular configuration/sample. According to the embodiments herein, the most desirable configuration/sample is the one with the greatest quantum efficiency percentage, which in FIG. 2C, is the top-most curve. In the embodiment shown in FIG. 2B, sample tray 50 is located at a fixed distance (e.g., approximately 2-5 inches) from three-way beam splitter 25. As described in further detail below, articulation platform 96 moves sample tray 50 along two axes to enable positioning of each solar cell 42 on the substrate/coupon 40 under the focused light beam while maintaining a fixed distance from three-way splitter 25.

Figure 2D:
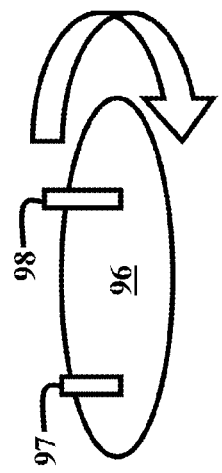
FIG. 2D illustrates a schematic diagram of the rotation of an articulation platform of a quantum efficiency measurement tool according to an embodiment herein.

Quantum efficiency measurement tool 80 may further include a transmittance detector 98 (along with probe module 97) on articulation platform 96 and under sample tray 50 to measure the transmittance of a thin film glass solar cell 42 on substrate 40 or the efficiency of an electrochromic material in another potential use of this tool 80 where multiple electrochromic materials are deposited and varied from one another on a combinatorial test substrate 40. In such an embodiment, articulation platform 96 rotates (e.g., as shown in FIG. 2D) to align the transmittance detector 98 under solar cell 42 on substrate 40 and three-way beam splitter 25. Transmittance is useful, for example, when developing electrochromic materials and therefore there is a need to shine light 25a through the substrate 40 to measure the transmittance of the electrochromic material.

FIG. 3A, with reference to FIGS. 1 through 2D, illustrates a schematic diagram of an unloaded sample tray 50 according to an embodiment herein. In addition, FIG. 3B, with reference to FIGS. 1 through 3A, illustrates a schematic diagram of a loaded sample tray 50 according to an embodiment herein. As shown in the embodiment of FIGS. 3A and 3B, sample tray 50 includes a support frame 82 to hold a solar cell substrate 40, where substrate 40 may include one solar cell 42 or multiple solar cells 42. According to one embodiment herein, when there are multiple solar cells 42 on substrate 40, each solar cell 42 is combinatorially varied. Substrate 40 is held in place by clamp 84, where clamp 84 is secured via channels 86. The channels 86 may be configured as a lip/ledge on which the substrate 40 rests, or the channels 86 may include vacuum-like properties to further retain the substrate 40 thereon. Operatively connected to support frame 82 are sample guides 88a, 88b, which are perpendicularly coupled to each other. In addition, while not shown in FIGS. 3A and 3B, in one embodiment, the sample tray 50 may be temperature controlled to regulate the temperature of the substrate 40 being tested. Substrate 40 is secured to the support frame 82 by positioning the substrate 40 at a corner 85 of the channels 86. The sample guide 88a moves axially and translationally with respect to sample guide 88b and the support frame 82 to accommodate different sizes of substrate 40. Once positioned on the sample guide 88a and aligned in the channel 86, the substrate 40 is locked in place with the clamp 84, which, in one embodiment, may use a vacuum (not shown) to further retain the substrate 40 in place.

Figure 4A:
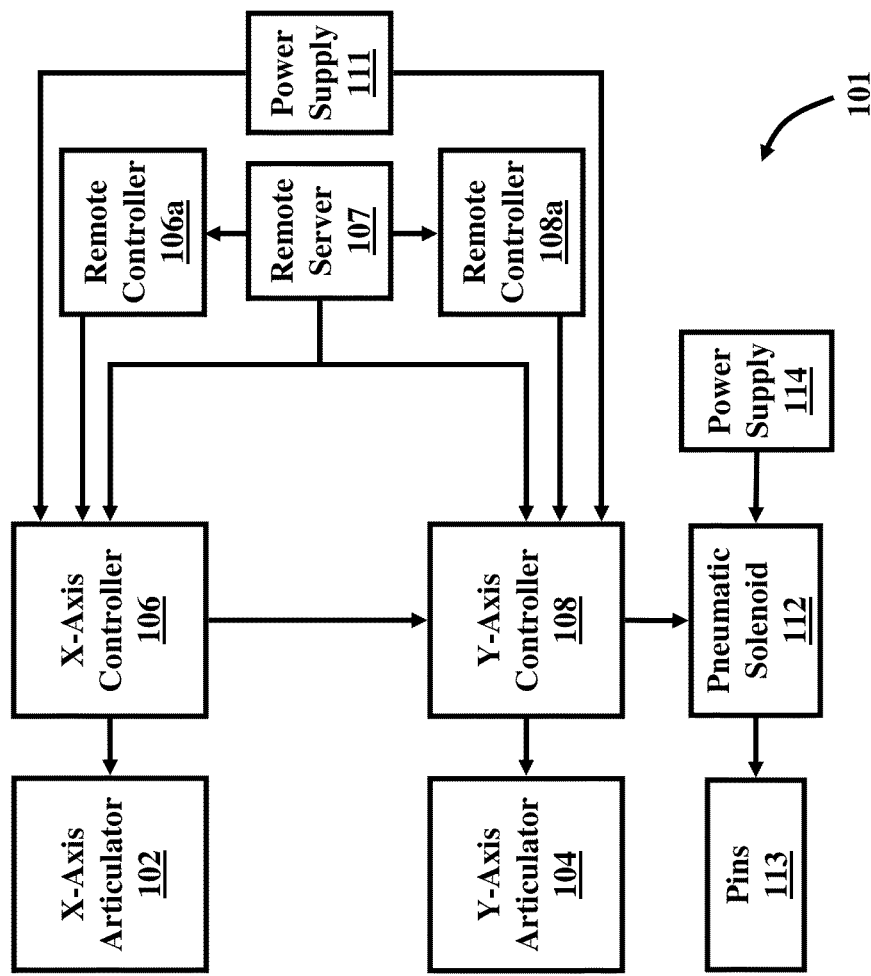
FIG. 4A illustrates a block diagram of an X-Y control device according to an embodiment herein.
Figure 4D:
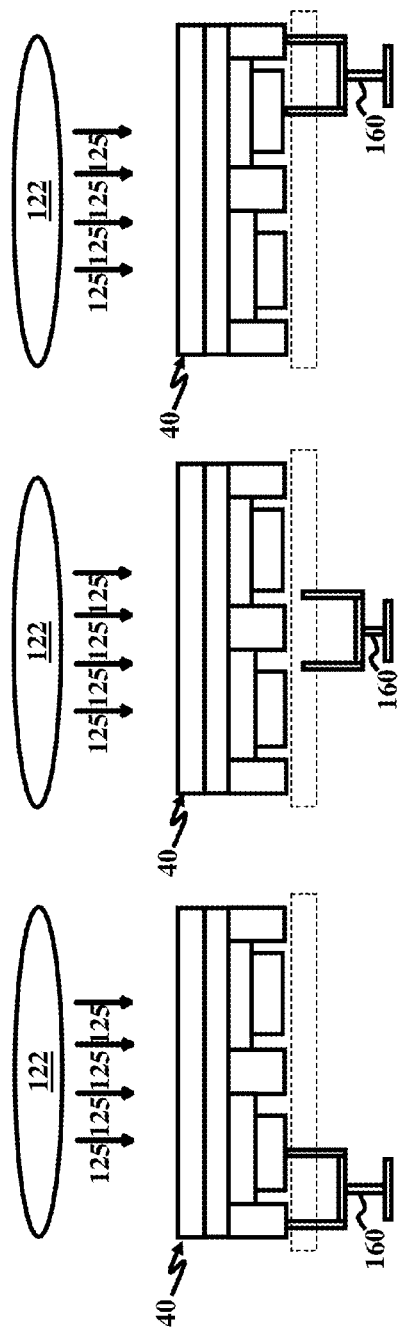
FIG. 4D illustrates a block diagram of a Z-stage combinatorial characterization apparatus in transition according to an embodiment herein.

FIG. 4A, with reference to FIGS. 1 through 3B, illustrates a block diagram of a multi-axis (e.g., X-Y) control device 101 according to an embodiment herein. The embodiments, as described herein, utilize the X, Y, and Z axes to define various geometric planes associated with the components described herein. Those skilled in the art would recognize that the X, Y, and Z axes may be configured in any suitable orientation, and the embodiments herein are not restricted to any particular orientation. As shown in FIG. 4A, multi-axis X-Y control device 101 includes an X-axis articulator 102 (e.g., a step motor), a Y-axis articulator 104 (e.g., a step motor), an X-axis controller 106 (e.g., SMC100CC controller available from Newport Corporation, Irvine, Calif., USA), an optional remote controller 106a, a Y-axis controller 108 (e.g., SMC100CC controller available from Newport Corporation, Irvine, Calif., USA), an optional remote controller 108a, a power supply 111, a pneumatic solenoid 112, and a solenoid power supply 114. According to one embodiment herein, remote controllers 106a and 108a are operatively coupled to a remote server 107 to allow remote control and automation of X-axis controller 106 and Y-axis controller 108, respectively. In addition, according to one embodiment herein, pneumatic solenoid 112 is coupled to a plurality of pins 113, which articulate in the Z-direction (via pneumatic solenoid 112) to form electrical connections to substrate 40 on articulation platform 96. The pins 113 may be configured as push-pins that include a spring at the tip to press against the electrodes of the substrate 40, or they may be sharp tipped stiff pins, or any other type of suitable probe. As shown in FIG. 4A, pneumatic solenoid 112 as well as X-axis controller 106 and Y-axis controller 108 are coupled to power supplies (i.e., power supply 111). While shown in FIG. 4A as one power supply 111, embodiments herein are not limited to such a configuration and those of ordinary skill in the art could provide a separate power supply connected to each of the X-axis controller 106 and Y-axis controller 108, respectively. Furthermore, power supply 111 and power supply 114 could also be consolidated into a single power supply unit to provide power to the X-axis controller 106, Y-axis controller 108, and pneumatic solenoid 112.

Moreover, according to one embodiment herein, X-Y control device 101 is operatively coupled to articulation platform 96 and sample tray 50 in order to move tray 50 (shown in FIG. 2B) along an X-axis and/or along a Y-axis. In so doing, X-Y control device 101 moves substrate 40 (shown in FIGS. 2A through 3B) along a plane that is located at a fixed distance from three-way beam splitter 25 (shown in FIGS. 2A and 2B) to vertically align specially treated portions of substrate 40 (e.g., solar cell 42) with three-way beam splitter 25. In one embodiment, the light 25a is blocked by a shutter (not shown) while the substrate 40 is moved to test each of the solar cells 42. Blocking the light 25a during movement of articulation platform 96 may serve to minimize heating of the substrate 40 and to also increase the accuracy of the data because the light 25a is only shone onto the solar cells 42 at one similar location on the cells 42 for each of the cells 42.

FIG. 4B, with reference to FIGS. 1 through 4A and 6, illustrates a block diagram of a multi-pin combinatorial characterization apparatus according to an embodiment herein. As shown in FIG. 4B, multi-pin combinatorial characterization apparatus 5a includes a lamp 122, light 125 (emitted from lamp 122), substrate 40, probes 145, switching matrix 150, programmable switch box 155, and computing device 70. Substrate 40, according to one embodiment, includes glass 133, a transparent conducting oxide (TCO) coating 135, electrodes 140a, 140b, and solar cell 42. Also shown in the embodiment of FIG. 4B, the electrodes (e.g., electrodes 140a, 140b) are transferred to a back surface (e.g., TCO 135) of substrate 40 where substrate 40 is not exposed to light (e.g., light 125 emitted from lamp 122). In the embodiment shown in FIG. 4B, each solar cell 42 of substrate 40 can be processed under varied wet (e.g. texturing) or dry (electrode sputtering, absorb layer deposition) conditions during the combinatorial processing (e.g., primary screening (110), shown in FIG. 1). In the embodiment shown in FIG. 4B, the area inside solar cell 42 includes a positive electrode 140a while the area outside of solar cell 42 is connected to a common electrical ground (e.g., electrode 140b). According to one embodiment herein, electrodes 140a, 140b are formed by chemical vapor deposition (CVD) and isolated by a light scribing process on substrate 40.

In addition, as shown in FIG. 4B, electrodes 140a, 140b are connected to a selective circuit (e.g., switching matrix 150). In one embodiment herein, a connection between electrodes 140a and 140b is made through switching matrix 150, which is designed to match the geometry of substrate 40 with at least one probe 145 touching the inside of each solar cell 42 (e.g., using electrode 140a) and the other touching the nearby outside of each solar cell 42 (e.g., using electrode 140b). For example, switching matrix 150 may include a plurality of probes 145, where each probe 145 includes a spring load pin (e.g., pin 113 shown in FIG. 4A) used for better contact and reduced series resistance. In addition, substrate 40 is seated on a substrate support structure 150a and may include, for example, articulation platform 96 shown in FIG. 2B and held in place by vacuum or by mechanical means, such as a clamp 84, or a combination of both. With a computing device 70 operatively connected to a selective circuit (e.g., as defined by the contacts made by electrode 140a and 140b on substrate 40), a control program (e.g., as stored and executed by a computing device 70, shown in FIG. 6) automatically selects one site (e.g., solar cell 42) on substrate 40 for testing and may continue in series with the next site (e.g., another solar cell 42) until all the sites on substrate 40 are tested.

FIG. 4C, with reference to FIGS. 1 through 4B and 6, illustrates a block diagram of a Z-stage combinatorial characterization apparatus 5b according to an embodiment herein. As shown in FIG. 4C, Z-stage combinatorial characterization apparatus 5b includes a lamp 122, light 125 (emitted from lamp 122), substrate 40, probes 145, Z-Stage device 160, and computing device 70. Z-stage combinatorial characterization apparatus 5b also includes an X-Y stage 150b (e.g., articulation platform 96) that moves along a plane defined by an X-axis and a Y-axis (e.g., as indicated in FIG. 4A). As described above, substrate 40, according to one embodiment, includes glass 133, a transparent conducting oxide (TCO) coating 135, electrodes 140a, 140b, and a solar cell 42. In the embodiment of FIG. 4C, all the electrodes (e.g., electrodes 140a, 140b) are transferred to a back surface (e.g., TCO 135) of substrate 40 where substrate 40 is not exposed to light (e.g., light 125, emitted from lamp 122). In the embodiment shown in FIG. 4C, each solar cell 42 of substrate 40 can be processed under varied wet (e.g. texturing) or dry (electrode sputtering, absorb layer deposition) conditions during the combinatorial processing (e.g., primary screening (110), shown in FIG. 1). In the embodiment shown in FIG. 4C, the area inside of solar cell 42 includes a positive electrode 140a while the area outside of solar cell 42 is the common electrical ground (e.g., electrode 140b). According to one embodiment herein, electrodes 140a, 140b are formed by CVD and isolated by a light scribing process on substrate 40.

In addition, as shown in FIG. 4C, electrodes 140a, 140b are connected to a selective circuit (e.g., Z-stage device 160). In one embodiment herein, a connection between electrodes 140a and 140b is made through Z-stage device 160, which includes a plurality of probes 145 (e.g., two probes 145 are shown in FIG. 4C) where at least one probe 145 touches the inside of each solar cell 42 (e.g., electrode 140a) and another probe 145 touches the nearby outside of each solar cell 42 (e.g., electrode 140b). In addition, as above, X-Y stage 150b and substrate 40 can be held together by vacuum or by mechanical means, such as a clamp 84, or a combination of both. With computing device 70 operatively connected to a selective circuit (e.g., as defined by the contacts made by electrode 140a and 140b on substrate 40), a control program (e.g., as stored and executed by computing device 70 shown in FIG. 6) automatically selects one region (e.g., solar cell 42) on substrate 40 for testing and may continue in series with the next site (i.e., solar cell 42) until all the sites on substrate 40 are tested.

In FIG. 4C, instead of the geometry-matched switching matrix 150 of multi-pin combinatorial characterization apparatus 5a shown in FIG. 4B, only two probes 145 attached to Z-stage device 160 are used with one probe 145 touching the area inside of the solar cell 42 and the other probe 145 contacting the area outside of the solar cell 42. Substrate 40 is also mounted on X-Y stage 150b for movement along an X-Y plane (in contrast to the stationary substrate support structure of multi-pin combinatorial characterization apparatus 5a shown in FIG. 4B) and probes 145 are fixed onto Z-stage device 160 to provide movement along a Z plane. After finishing testing solar cell 42, Z-stage device 160 lowers probes 145 to disconnect probes from electrodes 140a, 140b. Substrate 40 is then moved to the next site (as above) using X-Y stage 150b and the connection to electrodes 140a, 140b is restored (as shown in the sequential diagram in FIG. 4D).

Figure 4E:
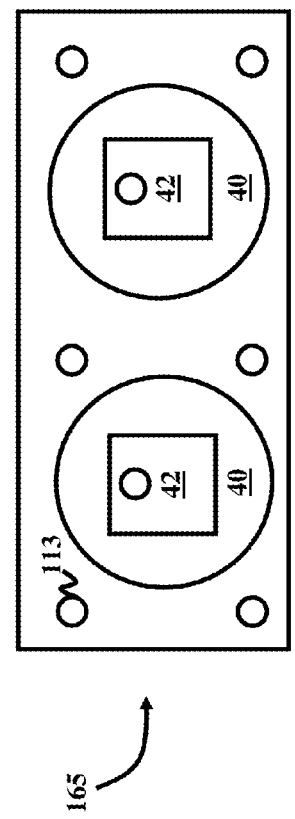
FIG. 4E illustrates a view of a probe fixture according to an embodiment herein.

The multi-pin combinatorial characterization apparatus 5a shown in FIG. 4B may be used for parallel testing. The Z-stage combinatorial characterization apparatus 5b shown in FIG. 4C also has good site-to-site repeatability because the light 125 (e.g., emitted from lamp 122) is fixed. These embodiments may also be universal for any kind of test substrate 40 and no specific fixture is required, particularly for the Z-stage combinatorial characterization apparatus 5b shown in FIG. 4C. Besides the automation, multi-pin combinatorial characterization apparatus 5a can also significantly increase throughput by enabling parallel testing. FIG. 4E, with reference to FIGS. 1 through 4D, illustrates a schematic top view diagram of a probe fixture 165 according to an embodiment herein. FIG. 4E shows that probe fixture 165 includes pins 113, which are used during the IQE and EQE test of solar cells 42 residing on substrate 40 (as described above). As shown in FIG. 4E, according to embodiments herein, simultaneous IQE and EQE testing can be automated and the solar cells 42 of a test substrate 40 may be tested in parallel. Consequently, the embodiments herein increase throughput on characterization significantly over the conventional methods where an operator is manually required to measure each sample.

In addition, a characterization tool based on multi-pin combinatorial characterization apparatus 5a or Z-stage combinatorial characterization apparatus 5b can optionally measure the temperature of solar cell 42 currently being measured, and correct for any temperature increase that occurs (e.g., due to expose of light 125 from lamp 122) of substrate 40. Alternatively, substrate 40 may be cooled during the characterization of the solar cell 42 to maintain a steady temperature during each measurement. For example, in one embodiment, a heat sink (not shown) may be used to cool substrate 40. In yet another alternate embodiment, substrate 40 can be pre-heated to a temperature sufficient to mitigate any ancillary heating, caused by the lamp 122 used during the IQE and EQE measurements, insignificant.

Specially treated portions of substrate 40 (e.g., solar cell 42) may include portions prepared using combinatorial processing. Combinatorial processing provides rapid evaluation of solar processing operations and materials. Some exemplary solar processing operations include, for example, operations for adding (depositions) and removing layers (etching), defining features, preparing layers (e.g., cleans), doping, etc. In such an embodiment, the systems supporting the combinatorial processing are flexible to accommodate the demands for running the different processes either in parallel, serial or some combination of the two. It is to be understood that the embodiments herein are not limited to the combinatorial development and testing of solar cells 42, but may also be used to test electrochromic materials, photochromic materials, thermochromic materials, etc.

As used herein, combinatorial processing may include any processing (e.g., solar cell processing) that varies the processing conditions in two or more regions of a substrate 40. A substrate 40 may be, for example, a silicon substrate 40 such as a coupon that is used in solar processing. A region of a substrate 40 may be any portion of the substrate 40 that is somehow defined, for example by dividing the substrate 40 into regions having predetermined dimensions or by using physical barriers, such as sleeves, over the substrate 40. The region may or may not be isolated from other regions. For example, a substrate 40 may be divided into two or more regions, each of which may or may not include solar cell structures 42 (e.g., $Cu_2ZnSnS_4$ solar cell structures and copper indium gallium selenide solar cell structures may occupy separate regions).

A process may be performed at each of the regions. For example, a first region is cleaned using a first cleaning agent, and a second region is cleaned using a second cleaning agent. The efficacies of the two cleaning agents are evaluated, and none, one, or both of the cleaning agents may be selected as suitable candidates for larger scale processing (e.g., on regions with structures, or regions enabling more sophisticated testing, or a full substrate, etc.). According to other examples, multiple iterations of the same experiment are performed on the same substrate 40, and any number of regions may be defined. For example, five cleaning solutions may be tested using fifteen regions of a substrate 40, each cleaning solution being tested three times.

FIG. 5, with reference to FIGS. 1 through 4E, illustrates a flow diagram according to an embodiment herein. Step (170) of the method of FIG. 5 provides a solar cell 42 that may be within a substrate 40 for measurement (e.g., using quantum efficiency measurement tool 80 shown in FIG. 2B). Step (175) aligns a solar cell 42 (e.g., using X-Y control device 101 shown in FIG. 4A) beneath the measurement apparatus (e.g., quantum efficiency measurement tool 80 shown in FIG. 2B). Next, step (180) applies a tuned wavelength of light 25a (e.g., using emitter 92 shown in FIG. 2B) to the aligned solar cell 42 on a substrate 40 that includes at least one solar cell 42 (as shown in FIGS. 2A and 2B). Step (185) of the method shown in FIG. 5 then simultaneously measures absorbed (e.g., light 25a, as absorbed by solar cell 42 on substrate 40, and measured using source meter 55 shown in FIG. 2A) and reflected light (e.g., light 40a, reflected from solar cell 42 and passing through three-way beam splitter 25 to become light 40b and detected using reflectance detector 30 shown in FIG. 2A) to calculate an IQE and EQE measurement (e.g., using computing device 70 shown in FIGS. 2A and 6) therefrom.

Figure 6:
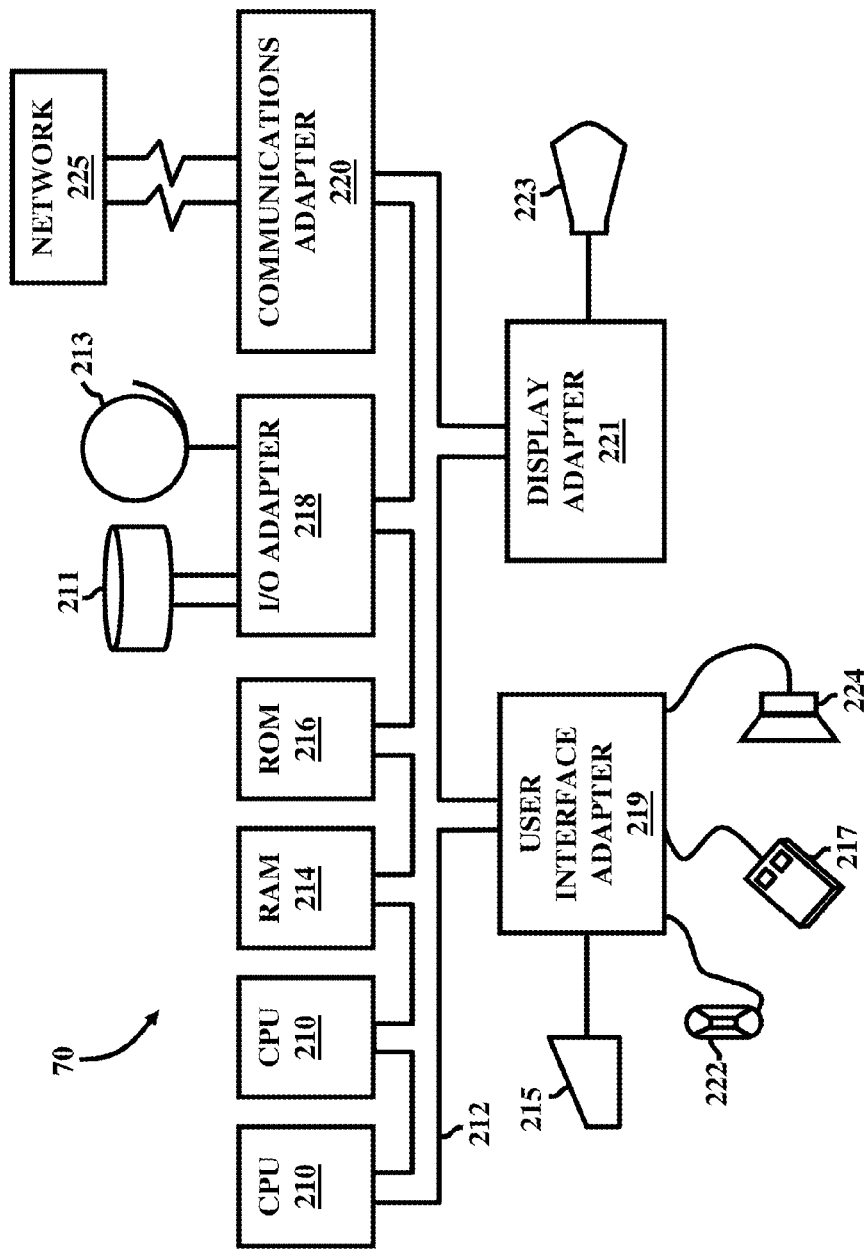
FIG. 6 illustrates a computing system according to an embodiment herein.

A representative hardware environment for practicing the embodiments herein is depicted in FIG. 6. This schematic drawing illustrates a hardware configuration of an information handling/computer system (e.g., computing device 70 of FIG. 2A) in accordance with the embodiments herein. The system comprises at least one processor or central processing unit (CPU) 210. The CPUs 210 are interconnected via system bus 212 to various devices such as a random access memory (RAM) 214, read-only memory (ROM) 216, and an input/output (I/O) adapter 218. The I/O adapter 218 can connect to peripheral devices, such as disk units 211 and tape drives 213, or other program storage devices that are readable by the system. The system can read the inventive instructions on the program storage devices and follow these instructions to execute the methodology of the embodiments herein. The system further includes a user interface adapter 219 that connects a keyboard 215, mouse 217, speaker 224, microphone 222, and/or other user interface devices such as a touch screen device (not shown) to the bus 212 to gather user input. Additionally, a communication adapter 220 connects the bus 212 to a data processing network 225, and a display adapter 221 connects the bus 212 to a display device 223 which may be embodied as an output device such as a monitor, printer, or transmitter, for example.

Embodiments herein provide a measurement tool 80 that permits a sample (e.g., as prepared using combinatorial processes) to be loaded once and all other testing functions in association with internal quantum efficiency measurement and external quantum efficiency measurement to be automated. In addition, such automation provides greater efficiency (e.g., less time to conduct the measurements because both the internal quantum efficiency measurement and external quantum efficiency measurement are performed simultaneously) over conventional systems, which would be advantageous for any research and development but may be of particular value in improving the throughput for combinatorial testing. The speed at which the solar cells 42 are characterized is valuable in achieving high performance combinatorial processing. Embodiments herein also provide greater precision (e.g., taking a reference measurement simultaneous to take the measurement of the internal quantum efficiency and external quantum efficiency) and greater accuracy (e.g., reducing noise in the measurement through a lock-in amplifier 65).

One embodiment of the combinatorial screening process described above (e.g., FIG. 1) enables multiple experiments to be performed on a single substrate 40 and the rapid evaluation of solar cell processing operations and solar cell materials. Multiple solar cells 42 may reside on a singe substrate 40 and are designed to run the different combinatorial processes either in parallel, serial, or some combination of the two. For example, embodiments herein allow forming different types of thin film solar cells, CZTS solar cells, CIGS solar cells, and cadmium telluride (CdTe) solar cells that can be combinatorially varied and evaluated. These methodologies all incorporate the formation of site-isolated regions using a combinatorial processing tool and the use of these site-isolated regions to form the solar cell area. Therefore, multiple solar cells 42 may be rapidly formed on a single substrate 40 for use in combinatorial methodologies. Any of the individual processes of the methods described herein may be varied combinatorially to test varied process conditions or materials.

The use of combinatorial-based rapid device prototyping methods (e.g., as shown in FIG. 1) permits fabrication, comprehensive characterization, and analysis of hundreds of unique solar cells 42 on a weekly basis to dramatically increase learning rates. Alternative device structures, process integration schemes, and material compositions are systematically explored at speeds that would otherwise be impossible using traditional methods and tools. This pace of development applied to Earth-abundant TFPV devices may represent an order of magnitude acceleration of R&D in this area.

For example, CZTS is a compound semiconductor that evolves from the chalcopyrite structured I-III-VI2 compound CIGS, where indium/gallium is substituted by zinc/tin and selenium by sulfur. The substituted elements in CZTS are comparatively orders of magnitude more abundant than CIGS elements. CZTS has a band gap between approximately 1.45 and 1.6 eV, which is very close to the optimum value of an absorber layer of a solar cell 42. Additionally, the band edge absorption coefficient of CZTS is above $1 \times 10^4$ $cm^{-1}$ which enables its use as a thin film solar cell absorber candidate.

A standard CZTS device structure may include the deposition of four primary layers on a substrate: a back contact (e.g., Mo), an absorber layer (e.g., CZTS), a buffer layer (e.g., CdS or ZnS), and a front contact (e.g., ITO or Al:ZnO). Each material and deposition process provides an opportunity to reduce manufacturing costs and increase cell efficiencies by using the combinatorial process described herein. Moreover, the similarity in process flow relative to current CIGS processes offers the intriguing possibility of retrofitting legacy production assets to produce lower cost devices using more environmentally friendly, Earth-abundant materials.

Various techniques can be used for depositing the CZTS absorber layer, which is the most critical layer in the device stack. These techniques include electron beam deposition continued by sulfurization, hybrid sputtering, vacuum evaporation with sulfurization, sol-gel followed by $H_2Se$ annealing, pulsed laser deposition, sputtering followed by sulfurization, single step RF sputtering, electroplating, and spray pyrolysis.

As described above, the embodiments herein improve the combinatorial screening and the characterization of compounds (e.g., CIGS absorption layers, CZTS absorption layers, and other chalcopyrite structured I-III-VI2 compound CIGS absorption layers) after the application of those formulations. For example, during an initial screening (e.g., primary screening process ((110)) shown in FIG. 1), many samples (e.g., 18 spots or 46 spots on a single wafer, where each spot is a unique material composition) are created using blanket films (e.g., as supplied by Advantiv Technologies, Inc. Fremont Calif., USA) and thereafter tested. This initial screening (e.g., primary screening process (110)) may have a simple criteria (e.g., maximizing external/internal quantum efficiency for a narrow wavelength band) to allow a quick evaluation and thereby quickly rule out materials that will not undergo the second stage of testing (e.g., in secondary screening process ((120)) shown in FIG. 1). During the secondary screening process ((120)) shown in FIG. 1, a variety of more specific characterization methods may be performed on the test cleaning formulations identified in primary screening process ((110)) on fabricated patterned/metallized surfaces. Such characterization methods include parametric tests and reliability tests. Sample criteria to evaluate include, but are not limited to: maximizing current density, maximizing external/internal quantum efficiency for a narrow wavelength band, and maximizing external/internal quantum efficiency for the bandwidth of sunlight.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of several embodiments, those skilled in the art will recognize that the embodiments herein can be practiced with modification within the spirit and scope of the appended claims.

What is claimed is:

1. A method for measuring quantum efficiency, said method comprising:
    providing a solar test substrate,
        the solar test substrate comprising multiple site isolated devices,
    wherein the multiple site isolated devices are combinatorially varied;
    emitting light from an emitter;
    splitting said light from the emitter into solar cell light and reference light,
    wherein said solar cell light strikes at least one of the multiple site isolated devices;
    detecting reflectance light,
    wherein said reflectance light comprises a portion of said solar cell light reflected from the at least one of the multiple site isolated devices on said solar test substrate;
    measuring a current from the at least one of the multiple site isolated devices; and
    simultaneously computing an internal quantum efficiency and an external quantum efficiency of the at least one of the multiple site isolated devices,
    wherein said internal quantum efficiency is calculated from the measured current and said external quantum efficiency is calculated from the detection of said reflectance light.

2. The method of claim 1, further comprising detecting said reference light, wherein the simultaneously computing said internal quantum efficiency and said external quantum efficiency comprises calculating said reference light as a reference to detect any drift between said reference and any of said reflectance light and said solar cell light.

3. The method of claim 2, further comprising extracting and amplifying a specific bandwidth of at least one of said reference light, said solar cell light, and said reflectance light.

4. The method of claim 1, wherein a sample tray automatically moves the solar test substrate on a horizontal plane to vertically align the solar test substrate under said solar cell light.

5. The method of claim 1, wherein the at least one of the multiple site isolated devices comprises multiple absorption layers, and wherein a white light bias controller is used to isolate the internal quantum efficiency and the external quantum efficiency of one of the multiple absorption layers from a remaining one or more of the multiple absorption layers.

6. The method of claim 1, further comprising cycling the light from the emitter through multiple wavelengths.

7. The method of claim 1, further comprising repeating the emitting, splitting, detecting, measuring, and simultaneously computing operations for remaining devices of the multiple site isolated devices on the solar test substrate and selecting a device having a highest external quantum efficiency.

8. The method of claim 7, further comprising moving the solar test substrate using an articulation platform supporting the solar test substrate to align each of the multiple site isolated devices with said solar cell light.

9. The method of claim 1, further comprising controlling the temperature of the solar test substrate.

10. The method of claim 1, wherein the multiple site isolated devices are processed under different wet conditions during combinatorial processing.

11. The method of claim 1, wherein electrodes of the multiple site isolated devices extend to a back side of the solar test substrate, the back side facing away from said solar cell light.

12. The method of claim 11, wherein the measuring operation comprises making electrical connections to the electrodes of the multiple site isolated devices using a switching matrix connected to a computing device.

13. The method of claim 12, wherein the switching matrix is electrically connected to two or more of the multiple site isolated devices.

14. The method of claim 13, wherein the two or more of the multiple site isolated devices connected to the switching matrix are tested in parallel such that said solar cell light strikes the two or more of the multiple site isolated devices at the same time.

15. The method of claim 11, wherein the measuring operation comprises aligning two or more contact pins with at least two electrical connections using a movable platform, and wherein the movable platform is connected to a computing device.

16. The method of claim 1, wherein the multiple site isolated devices comprise one or more copper indium gallium diselenide (CIGS) cells and one or more copper zinc tin sulfide (CZTS) cells.

17. The method of claim 1, wherein the multiple site isolated devices comprise a first site isolated device and a second site isolated device, wherein the first site isolated device is processed using a first cleaning agent, wherein the second site isolated device is processed using a second cleaning agent different from the first cleaning agent.

18. The method of claim 17, wherein the method comprises evaluating effects of the first cleaning agent and the second cleaning agent on the internal quantum efficiency and the external quantum efficiency.

19. The method of claim 1, wherein the method comprises combinatorial screening of the multiple site isolated devices on the solar test substrate.

* * * * *